United States Patent
Martin (10) Patent No.: US 9,522,247 B2
(45) Date of Patent: *Dec. 20, 2016

(54) METHOD OF TREATING A PATIENT HAVING PULMONARY HYPERTENSION BY LONG TERM NO THERAPY

(71) Applicant: L'Air Liquide, Société Anonyme pour l'Etude et l'Exploitation des Procédés Georges Claude, Paris (FR)

(72) Inventor: Andrew Martin, Wilmington, DE (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 519 days.

This patent is subject to a terminal disclaimer.

(21) Appl. No.: 13/930,435

(22) Filed: Jun. 28, 2013

(65) Prior Publication Data
US 2015/0000659 A1    Jan. 1, 2015

(51) Int. Cl.
*A61M 16/06* (2006.01)
*A61M 16/10* (2006.01)
(Continued)

(52) U.S. Cl.
CPC ..... *A61M 16/0672* (2014.02); *A61M 16/0666* (2013.01); *A61M 16/122* (2014.02);
(Continued)

(58) Field of Classification Search
None
See application file for complete search history.

(56) References Cited

U.S. PATENT DOCUMENTS 2,843,119 A * 7/1958 Glasser ............... A61D 7/04
128/205.17
3,513,844 A 5/1970 Smith
(Continued)

FOREIGN PATENT DOCUMENTS

EP    0 010 880    5/1980
EP    1 516 639    3/2005
(Continued)

OTHER PUBLICATIONS

Partial International Search Report for related PCT/US2014/044494, Oct. 2, 2014.
(Continued)

*Primary Examiner* — Lynne Anderson
*Assistant Examiner* — Joseph D Boecker
(74) *Attorney, Agent, or Firm* — Allen E. White (57) ABSTRACT

The invention concerns a nasal cannula assembly (10) adapted to deliver gases to a patient comprising a first compartment (1) and a second compartment (2) separated by a separation wall (6); a pair of nasal prongs (5) in fluid communication with the first compartment (1); the first compartment (1) comprising a first inlet (11) for introducing a first gas into said first compartment (1); the second compartment (2) comprising a second inlet (2) for introducing a second gas into said second compartment (2); and the separation wall (6) comprising at least one valve element (3) for controlling the passage of gas from the second compartment (2) to the first compartment (1). The invention concerns also a breathing assistance apparatus comprising a source of NO gas, and said nasal cannula assembly (10) in fluid communication with said source of NO gas.

10 Claims, 2 Drawing Sheets

(51) Int. Cl.
*A61M 16/12* (2006.01)
*A61M 16/20* (2006.01)
*A61M 16/08* (2006.01)

(52) U.S. Cl.
CPC ....... *A61M 16/208* (2013.01); *A61M 16/0866* (2014.02); *A61M 2202/0208* (2013.01); *A61M 2202/0275* (2013.01)

(56) References Cited

U.S. PATENT DOCUMENTS

| | | | | |
|---|---|---|---|---|
| 4,492,228 | A * | 1/1985 | Makovic | A61M 16/1075 128/207.17 |
| 4,535,767 | A | 8/1985 | Tiep et al. | |
| 5,558,083 | A | 9/1996 | Bathe et al. | |
| 5,732,693 | A | 3/1998 | Bathe et al. | |
| 5,873,359 | A | 2/1999 | Zapol et al. | |
| 6,016,802 | A * | 1/2000 | Jackson | A62B 9/02 128/201.19 |
| 6,051,241 | A | 4/2000 | Briend et al. | |
| 6,089,229 | A * | 7/2000 | Bathe | A61M 16/12 128/203.12 |
| 6,142,147 | A | 11/2000 | Head et al. | |
| 6,478,026 | B1 * | 11/2002 | Wood | A61M 16/0666 128/207.13 |
| 6,581,599 | B1 | 6/2003 | Stenzler | |
| 6,644,315 | B2 | 11/2003 | Ziaee | |
| 6,668,828 | B1 | 12/2003 | Figley et al. | |
| 7,328,703 | B1 * | 2/2008 | Tiep | A61M 16/0666 128/204.24 |
| 7,481,219 | B2 * | 1/2009 | Lewis | A61D 7/04 128/206.11 |
| 8,979,810 | B1 * | 3/2015 | Beyer | A61M 1/0023 604/173 |
| 2001/0019034 | A1 * | 9/2001 | Tai | F15C 5/00 216/8 |
| 2002/0017300 | A1 * | 2/2002 | Hickle | A61B 5/0836 128/204.22 |
| 2002/0078952 | A1 * | 6/2002 | Hopper | A61F 11/00 128/200.24 |
| 2003/0079749 | A1 * | 5/2003 | Strickland | A61M 16/0666 128/203.22 |
| 2003/0150458 | A1 * | 8/2003 | Arnott | A61M 16/06 128/204.18 |
| 2004/0060560 | A1 * | 4/2004 | Stenzler | A61M 16/06 128/206.21 |
| 2005/0205096 | A1 * | 9/2005 | Matula, Jr. | A61M 16/0666 128/207.11 |
| 2006/0266361 | A1 * | 11/2006 | Hernandez | A61M 16/06 128/206.11 |
| 2007/0144518 | A1 * | 6/2007 | Acker | A61B 5/0836 128/204.21 |
| 2008/0041393 | A1 * | 2/2008 | Bracken | A61M 16/0666 128/207.18 |
| 2008/0078393 | A1 * | 4/2008 | Acker | A61B 5/0836 128/204.29 |
| 2008/0142012 | A1 * | 6/2008 | Farnsworth | A61M 16/00 128/205.24 |
| 2008/0142013 | A1 * | 6/2008 | Hallett | A61M 16/06 128/205.24 |
| 2008/0142019 | A1 * | 6/2008 | Lewis | A61M 16/0666 128/207.18 |
| 2009/0260628 | A1 * | 10/2009 | Flynn, Sr. | A61M 16/0078 128/203.28 |
| 2011/0108041 | A1 * | 5/2011 | Sather | A61M 15/08 128/848 |
| 2011/0240035 | A1 * | 10/2011 | Gillies | A61M 16/0666 128/207.18 |
| 2012/0305001 | A1 * | 12/2012 | Tatkov | A61M 16/06 128/205.25 |
| 2013/0211275 | A1 * | 8/2013 | Curti | A61M 16/0666 600/543 |
| 2013/0245483 | A1 * | 9/2013 | Eichler | A61B 5/082 600/532 |
| 2014/0066801 | A1 * | 3/2014 | Tero | A61M 16/0666 600/543 |
| 2014/0130805 | A1 * | 5/2014 | Tiep | A61M 16/0672 128/207.18 |
| 2014/0150789 | A1 * | 6/2014 | Flanagan | A61M 16/0672 128/203.22 |
| 2014/0166009 | A1 * | 6/2014 | Flanagan | A61M 16/0677 128/203.22 |
| 2016/0030229 | A1 * | 2/2016 | Goldschmidt | A61F 5/56 128/847 |

FOREIGN PATENT DOCUMENTS

| | | |
|---|---|---|
| GB | 2 493 520 | 2/2013 |
| WO | WO 2005 099801 | 10/2005 |
| WO | WO 2010 076711 | 7/2010 |

OTHER PUBLICATIONS

Dumont, C.P. et al., "Using a reservoir nasal cannula in acute care," Critical Care Nurse, vol. 22, No. 4, Aug. 2002, pp. 41-46.

\* cited by examiner

METHOD OF TREATING A PATIENT HAVING PULMONARY HYPERTENSION BY LONG TERM NO THERAPY

BACKGROUND OF THE INVENTION

Field of the Invention

The invention concerns a nasal cannula assembly adapted to deliver gases to a patient, especially for NO gas therapy, a breathing assistance apparatus comprising such a nasal cannula assembly, and a method for treating pulmonary vasoconstriction in a patient using such a nasal cannula assembly and/or breathing assistance apparatus.

Description of the State of the Art

NO/nitrogen gas mixtures are commonly used for treating vasoconstrictions of the lung and pulmonary hypertension in adults and infants.

For instance, EP-A-1516639 discloses a gaseous mixture consisting of NO and an inert gas, preferably nitrogen, used for the production of an inhalable medicament for treating persistent pulmonary hypertension of the newborn.

Before being inhaled by the patient, the NO/$N_2$ mixture is generally diluted in an oxygen-containing gas, such as air or a $O_2/N_2$ mixture, comprising at least 21 vol. % of oxygen.

Typically, NO is present in the final mixture in an amount of several (1-800, most often 5-80) ppm in volume.

However, as NO is rapidly oxidized into $NO_2$ in the presence of oxygen, it is important to avoid long residence times in gas administration apparatus between the point of mixing of the NO/$N_2$ mixture with the oxygen containing gas and inhalation by the patient, in order to keep the concentration of $NO_2$ in said inhalable medicament at less than 5 ppm, ideally less than 1 ppm, in the inhaled gas mixtures because $NO_2$ is a highly toxic gas.

NO gas mixtures are delivered by modified ventilation devices or special modules added to standard ventilators. Such devices are well known and taught, for instance, by U.S. Pat. Nos. 5,558,083; 5,873,359; 5,732,693; and 6,051,241.

Current NO delivery systems are designed for use with ventilators or other breathing gas delivery devices in a hospital or transport setting. Systems to deliver NO to ambulatory patients are in development. The majority of delivery devices are pulsed, sequential, or proportional delivery systems that sense the start of patient inhalation and use one or more electronically controlled valves or switches to deliver a sequenced flow of NO to the patient interface, for example, an endotracheal tube, a facemask, or a nasal cannula.

For example, U.S. Pat. No. 6,089,229 discloses a device comprising sensing means for sensing the initiation of an inhalation of a patient and a delivery means responsive to the sensing means.

Further, U.S. Pat. No. 6,142,147 teaches an apparatus with a pressure sensor and a valve controller which is responsive to the pressure sensor, and which selectively connects a first port to a second port, said second port being connected to a source of NO gas, when a negative pressure event is sensed. Here the negative pressure event would be caused by a patient's inhalation so that again a means of sensing the patient's inhalation is used.

Furthermore, U.S. Pat. No. 6,581,599 deals with a method of delivering NO that includes detecting the onset of inspiration.

If adapted for NO delivery to ambulatory patients, such systems suffer from the requirements of a source of electrical power and the need for electromechanical parts to sense and administer sequenced pulses of NO, both of which increase the size of the system, and limit its portability. In addition, due to inevitable lags in timing between detection of the start of patient inhalation and operation of dosing valves, these systems risk delivering their pulses too late in the inhalation, such that a significant fraction of NO is exhaled.

However, there is sufficient evidence to suggest that long term NO therapy may be beneficial for some therapeutic indications, e.g. in treating pulmonary arterial hypertension. For these long term therapies, alternative delivery systems are needed for ambulatory patients. This is comparable to the need for devices for outpatient and in-home oxygen therapy.

For this purpose, a delivery system convenient for use by ambulatory patients, requiring a minimum of electromechanical parts, is required so that they can follow their NO treatment after they have left the hospital setting.

One common patient interface for home oxygen delivery is a standard form nasal cannula. Nasal cannulas are well known and widely used to deliver supplemental oxygen to patients suffering from a wide variety of respiratory and cardiovascular diseases. Generally, one end of an oxygen supply tubing is connected to a source of oxygen, and the other end of the tubing splits into two branches that meet to form a loop, where a set of two nasal prongs are positioned on that loop. The nasal prongs are inserted into a patient's nares, and a constant or time-pulsed flow of oxygen regulated by the source is sent through the tubing and the two branches of the loop so as to exit through the nasal prongs into the patient's nares. During inspiration, the patient inhales oxygen from the prongs together with entrained room air that is drawn through the space between the nasal prongs and the walls of the patient's nares. During exhalation, the patient exhales through the space between the nasal prongs and the walls of the patient's nares, and in the case of a constant oxygen supply flow, oxygen continues to exit into the patient's nares, such that much of this oxygen is carried with the expiratory flow into the surrounding room air. Pulsed oxygen delivery devices attempt to conserve oxygen by sensing the patient's breathing cycle, and then delivering a short-duration flow or pulse of oxygen through a nasal cannula only during inhalation, so as to avoid losing oxygen to the room air during exhalation.

As nasal cannulas are standard in the delivery of supplemental oxygen, many variants exist. For example, U.S. Pat. No. 4,535,767 to Tiep et al. describes an oxygen delivery apparatus consisting of a reservoir cannula, a version of which is available as a commercial product called the Oxymizer from Chad Therapeutics, as described, for example, by Dumont and Tiep (Using a reservoir nasal cannula in acute care; *Crit Care Nurse* 2002; 22:41-46). This reservoir cannula includes a chamber in fluid communication with both the oxygen supply line and nasal prongs. The chamber is enclosed in part by a flexible diaphragm that collapses upon inhalation so as to empty its contents through the nasal prongs while at the same time blocking flow from the oxygen supply line to the chamber. The flexible diaphragm then expands during exhalation to fill the chamber with exhaled gas while re-establishing flow from the oxygen supply line into the chamber, such that oxygen from the supply line mixes with and displaces the exhaled gas through the nasal prongs. This type of reservoir cannula has found utility in supplying supplemental oxygen to patients, but is ill-suited for supplying patients with NO/nitrogen gas mixtures in place of oxygen. First, reservoir cannulas as previously described contain means to connect to only a single source of gas; however because commercial NO/nitrogen gas mixtures contain no oxygen, patients may require an additional source of supplemental oxygen. Second, even if air entrained from the room during inhalation provides sufficient oxygen to meet a patient's demand, it is not acceptable that oxygen-containing gas exhaled by the patient mix with NO-containing gas supplied to the chamber. It is well known that NO and oxygen react over time to produce $NO_2$, which is toxic even at relatively low concentrations (e.g. above 5 ppm short term or even 1 ppm for long term), and as such it is well accepted that the residence time during which NO is brought into contact with oxygen should be minimized when supplying these gases to a patient. Finally, the Oxymizer cannula delivers 20 mL of oxygen to the patient each breath. For commonly supplied concentrations of medical NO/nitrogen gas mixtures (e.g. containing 800 ppm NO in balance nitrogen) this delivered volume risks exposing the patient to too high a concentration of NO and too low a concentration of oxygen, especially for younger patients with tidal volumes less than ~200 ml, or for adult patients exhibiting rapid, shallow breathing.

Another nasal cannula variant that exists is commonly referred to as a dual-lumen nasal cannula. For example, TeleFlex Hudson RCI Dual Lumen Cannulas are commercially available. These cannulas connect through tubing to a source of oxygen and to a pressure sensing instrument, both of which are in fluid communication with a pair of nasal prongs, the cross section of each prong being split into two sections (or lumen) by a wall, with one section in fluid communication with the source of oxygen, and the other section in fluid communication with the pressure sensing instrument. While it is possible that one could conceive of connecting a source of NO-containing gas in place of the pressure sensing instrument in order to supply both NO and oxygen simultaneously through the dual-lumen cannula, no reservoir, chamber, or other mechanism is included to control the flow of gases. To provide a pulsed delivery of NO, one would need to rely on the systems described above that sense the start of patient inhalation and use one or more electronically controlled valves or switches to deliver a sequenced pulse of NO.

BRIEF SUMMARY OF THE INVENTION

A main goal of the invention is to provide a delivery system convenient for use by ambulatory patients, which allows nitric oxide (NO) to be efficiently administered over extended time periods, i.e. hours, days, weeks, through nasal prongs in a manner that minimizes delivery into the anatomical dead volume at the end of inhalation, and therefore also minimizes exhalation of NO. In so doing, the system must avoid bringing NO-containing gas into contact with oxygen-containing gas until just prior to delivery to the patient, so as to avoid or minimize production of toxic $NO_2$ gas through reaction of NO with oxygen.

Another goal is to provide a delivery system that, in contrast to pulsed delivery systems described in prior art, does not require a sensor to detect the onset of inspiration nor any processing unit (such as a PLC or programmable computer) or other electronics.

A solution according to the present invention concerns a nasal cannula assembly adapted to deliver gases to a patient comprising:
 a first compartment and a second compartment separated by a separation wall,
 a pair of nasal prongs in fluid communication with the first compartment,
 the first compartment comprising a first inlet for introducing a first gas into said first compartment,
 the second compartment comprising a second inlet for introducing a second gas into said second compartment, and
 the separation wall comprising at least one valve element for controlling the passage of gas from the second compartment to the first compartment.

Depending on the embodiment, the nasal cannula assembly according to the present invention can comprise one or several of the following features:
 the separation wall comprises at least two valve elements.
 the first compartment comprises a first inlet forming a side gases entry in fluid communication with a gas transport conduct.
 the nasal cannula assembly further comprises a hollow body comprising an internal chamber comprising at least the first compartment.
 at least the first compartment is part of a hollow body forming a gas conduct or a manifold.
 said hollow body and said pair of nasal prong are integrally molded from a soft plastics material.
 the prongs are detachable from said hollow body to allow different sized prongs to be placed on said hollow body to suit different sized patients.
 the valve element(s) are one-way valve(s).
 a pair of valve elements is arranged in the separation wall, directly opposite the pair nasal prongs.
 the second compartment comprises a deformable wall.
 the second compartment forms a deformable-wall reservoir comprising an internal volume for the gas, when fully inflated, of about 0.5 to 5 ml.

The present invention also concerns a breathing assistance apparatus comprising:
 a source of NO-containing gas, and
 a nasal cannula assembly according to the present invention in fluid communication with said source of NO-containing gas.

Depending on the embodiment, the breathing assistance apparatus according to the present invention can comprise one or several of the following features:
 breathing assistance apparatus further comprises a source of an oxygen-containing gas in fluid communication with the nasal cannula assembly.
 said source of NO-containing contains NO and nitrogen.
 said source of NO-containing contains up to 3000 ppm in volume of NO in a balance of nitrogen.

The present invention also concerns a method for treating pulmonary vasoconstriction in a patient, comprising:
 a) providing a nasal cannula assembly according to the present invention, and
 b) providing a therapeutically-effective amount of a NO-containing gas to said patient through said nasal cannula assembly for inhalation.

Depending on the embodiment, the nasal cannula assembly according to the present invention can comprise one or several of the following features:
 the patient is an adult, an infant or a newborn.
 pulmonary vasoconstriction is associated with persistent pulmonary hypertension of the newborn.
 pulmonary vasoconstriction is associated with pulmonary arterial hypertension.
 the NO-containing gas is mixed with an oxygen-containing gas just before being inhaled by the patient.
 the NO-containing gas is a NO/nitrogen mixture.
 the NO-containing gas consists in a NO/nitrogen mixture containing up to 3000 ppm by volume of NO.

the $O_2$-containing gas is air or an $O_2/N_2$ mixture containing at least 21 vol. % of $O_2$.

The invention may be further defined in some embodiments by one or more of the following numbered sentences:

1. A method for treating pulmonary vasoconstriction in a patient, comprising:
   a) providing a nasal cannula assembly (10) adapted to deliver gases to a patient, the nasal cannula assembly (10) comprising:
      A) a hollow body (4) configured to be capable of acting as a gas conduct or a gas manifold and comprising an internal chamber (7) defining a first compartment (1),
      B) the first compartment (1) and a second compartment (2) separated by a separation wall (6),
      C) a pair of nasal prongs (5) in fluid communication with the first compartment (1),
      D) the first compartment (1) comprising a first inlet (11) forming a side gases entry in fluid communication with a gas transport conduct and configured to conduct a first gas into said first compartment (1),
      E) the second compartment (2) having a fully inflated internal volume for a gas of about 0.5 to 5 ml, the second compartment (2) comprising,
         a second inlet (12) configured to conduct a second gas into said second compartment (2), and
         a deformable wall (14),
      F) the separation wall (6) comprising at least two, one-way, duckbill or umbrella valves (3) having a cracking pressure of 0.5 kPa or less which are oriented and arranged in the separation wall (6) directly opposite the pair nasal prongs (5) to thereby be capable of
         permitting a passage of gas from the second compartment (2) to the first compartment (1) and
         preventing or limiting a passage of gas from the first compartment (1) to the second compartment (2),
   b) providing a source of NO-containing gas having from 1 ppm to 5000 ppm in volume of NO in a balance of nitrogen in fluid communication with the nasal cannula assembly (10),
   c) providing a source of an oxygen-containing gas containing at least 21% (by volume) of $O_2$ in fluid communication with the nasal cannula assembly (10), and
   d) providing a therapeutically-effective amount of a NO-containing gas to said patient through said nasal cannula assembly for inhalation to thereby provide the patient with the therapeutically effective amount of the NO-containing gas.

2. A method for treating pulmonary vasoconstriction in a patient, comprising:
   a) providing a nasal cannula assembly (10) in fluid communication with said source of NO-containing gas, wherein the nasal cannula assembly (10) comprises:
      A) a first compartment (1) and a second compartment (2) separated by a separation wall (6),
      B) a pair of nasal prongs (5) in fluid communication with the first compartment (1),
      C) the first compartment (1) comprising a first inlet (11) configured to conduct a first gas into said first compartment (1),
      D) the second compartment (2) comprising a second inlet (2) configured to conduct a second gas into said second compartment (2), and
      E) the separation wall (6) comprising at least one valve element (3) configured to
         permit the passage of gas from the second compartment (2) to the first compartment (1) and
         prevent or limit the passage of gas from the first compartment (1) to the second compartment (2), and
   b) providing a therapeutically-effective amount of a NO-containing gas to said patient through said nasal cannula assembly for inhalation to thereby provide the patient with the therapeutically effective amount of the NO-containing gas.

3. The method according to Numbered Sentence 1 or 2, wherein the patient is an adult, an infant or a newborn.

4. The method according to Numbered Sentence 1, 2 or 3, wherein the patient has pulmonary vasoconstriction associated with persistent pulmonary hypertension of the newborn.

5. The method according to Numbered Sentence 1, 2, 3 or 4, wherein the patient has pulmonary vasoconstriction is associated with pulmonary arterial hypertension.

6. The method according to Numbered Sentence 1, 2, 3, 4 or 5, wherein the NO-containing gas is mixed with an oxygen-containing gas just before being inhaled by the patient.

7. The method according to Numbered Sentence 1, 2, 3, 4, 5 or 6, wherein the NO-containing gas is a NO/nitrogen mixture.

8. The method according to Numbered Sentence 1, 2, 3, 4, 5, 6 or 7, wherein the NO-containing gas consists in a NO/nitrogen mixture containing from 1 ppm to 5000 ppmv of NO.

9. The method according to Numbered Sentence 1, 2, 3, 4, 5, 6, 7 or 8, wherein the $O_2$-containing gas is air or an $O_2/N_2$ mixture containing at least 21% (by volume) of $O_2$.

10. The method according to Numbered Sentence 1, 2, 3, 4, 5, 6, 7, 8 or 9, wherein the separation wall (6) comprises at least two valve elements (3).

11. The method according to Numbered Sentence 1, 2, 3, 4, 5, 6, 7, 8, 9 or 10, wherein the first compartment (1) comprises a first inlet (11) forming a side gases entry in fluid communication with a gas transport conduct.

12. The method according to Numbered Sentence 1, 2, 3, 4, 5, 6, 7, 8, 9, 10 or 11, wherein the nasal cannula assembly further comprises a hollow body (4) comprising an internal chamber (7) comprising at least the first compartment (1).

13. The method according to Numbered Sentence 1, 2, 3, 4, 5, 6, 7, 8, 9, 11 or 12, wherein at least the first compartment (1) is part of a hollow body (4) configured to be capable of acting as a gas conduct or a gas manifold.

14. The method according to Numbered Sentence 1, 2, 3, 4, 5, 6, 7, 8, 9, 10, 11, 12 or 13, wherein the hollow body (4) and said pair of nasal prong (5) are integrally molded from a soft plastics material.

15. The method according to Numbered Sentence 1, 2, 3, 4, 5, 6, 7, 8, 9, 10, 11, 12, 13 or 14, wherein the prongs (5) are detachable from said hollow body (4) and selected from different sized prongs suitable for different sized patient nares.

16. The method according to Numbered Sentence 1, 2, 3, 4, 5, 6, 7, 8, 9, 10, 11, 12, 13, 14 or 15, wherein the valve elements (3) are one-way valves.

17. The method according to Numbered Sentence 1, 2, 3, 4, 5, 6, 7, 8, 9, 10, 11, 12, 13, 14, 15 or 16, wherein a pair of valve elements (3) is arranged in the separation wall (6), directly opposite the pair nasal prongs (5).

18. The method according to Numbered Sentence 1, 2, 3, 4, 5, 6, 7, 8, 9, 10, 11, 12, 13, 14, 15, 16 or 17, wherein the second compartment (2) comprises a deformable wall (14).

19. The method according to Numbered Sentence 1, 2, 3, 4, 5, 6, 7, 8, 9, 10, 11, 12, 13, 14, 16, 17 or 18, wherein the second compartment (2) forms a deformable-wall reservoir comprising a fully inflated internal volume for the gas of about 0.5 to 5 ml.

20. The method according to Numbered Sentence 1, 2, 3, 4, 5, 6, 7, 8, 9, 10, 11, 12, 13, 14, 16, 17, 18 or 19, wherein the nasal cannula assembly does not comprise a sensor configured to detect an onset of patient inspiration.

21. The method according to Numbered Sentence 1, 2, 3, 4, 5, 6, 7, 8, 9, 10, 11, 12, 13, 14, 16, 17, 18, 19 or 20, wherein the valve (3) is selected from an umbrella valve or a duckbill valve.

22. The method according to Numbered Sentence 1, 2, 3, 4, 5, 6, 7, 8, 9, 10, 11, 12, 13, 14, 16, 17, 18, 19, 20 or 21, wherein the valve (3) has a cracking pressure of 0.5 kPa or less.

23. The method according to Numbered Sentence 1, 2, 3, 4, 5, 6, 7, 8, 9, 10, 11, 12, 13, 14, 16, 17, 18, 19, 20, 21 or 22, wherein the reservoir (2) has a greater Compliance while filling than when the reservoir (2) is full.

24. The method according to Numbered Sentence 1, 2, 3, 4, 5, 6, 7, 8, 9, 10, 11, 12, 13, 14, 16, 17, 18, 19, 20, 21, 22, or 23, wherein the nasal prongs (5) includes an external pillow element (8) at an end.

25. The method according to Numbered Sentence 24, wherein the pillow elements (8) is made of silicone.

26. The method according to Numbered Sentence 1, 2, 3, 4, 5, 6, 7, 8, 9, 10, 11, 12, 13, 14, 16, 17, 18, 19, 20, 21, 22, 23, 24 or 25, wherein the nasal cannula assembly further comprises an expiratory orifice (13), optionally comprising an additional one-way expiratory valve, between the first compartment (1) defining an internal chamber (7) and an external atmosphere.

27. The method according to Numbered Sentence 1, 2, 3, 4, 5, 6, 7, 8, 9, 10, 11, 12, 13, 14, 16, 17, 18, 19, 20, 21, 22, 23, 24, 25 or 26, wherein the nasal cannula assembly further comprises a resistive element (9) between an internal volume (7) of the first compartment (1) and an air or oxygen supply (11), the resistive element configured to ensure a sufficient pressure drop upon the onset of inhalation to open at least one valve element (3).

The invention may be further defined in some embodiments by one or more of the following numbered sentences:

1. Nitric Oxide for use in the treatment of pulmonary vasoconstriction by inhalation from a nasal cannula assembly (10) adapted to deliver gases to a patient, the nasal cannula assembly (10) comprising:
    A) a hollow body (4) configured to be capable of acting as a gas conduct or a gas manifold and comprising an internal chamber (7) defining a first compartment (1),
    B) the first compartment (1) and a second compartment (2) separated by a separation wall (6),
    C) a pair of nasal prongs (5) in fluid communication with the first compartment (1),
    D) the first compartment (1) comprising a first inlet (11) forming a side gases entry in fluid communication with a gas transport conduct and configured to conduct a first gas into said first compartment (1),
    E) the second compartment (2) having a fully inflated internal volume for a gas of about 0.5 to 5 ml, the second compartment (2) comprising,
        a second inlet (12) configured to conduct a second gas into said second compartment (2), and
        a deformable wall (14),
    F) the separation wall (6) comprising at least two, one-way, duckbill or umbrella valves (3) having a cracking pressure of 0.5 kPa or less which are oriented and arranged in the separation wall (6) directly opposite the pair nasal prongs (5) to thereby be capable of permitting a passage of gas from the second compartment (2) to the first compartment (1) and preventing or limiting a passage of gas from the first compartment (1) to the second compartment (2),
    c) the nasal cannula assembly (10) fluidly connected to a source of NO-containing gas having from 1 ppm to 5000 ppm in volume of NO in a balance of nitrogen, and
    d) the nasal cannula assembly (10) fluidly connected to a source of an oxygen-containing gas containing at least 21% (by volume) of $O_2$ in fluid communication with the nasal cannula assembly (10).

2. Nitric Oxide for use in the treatment of pulmonary vasoconstriction by inhalation from a nasal cannula assembly (10), wherein the nasal cannula assembly (10) comprises:
    a) a first compartment (1) and a second compartment (2) separated by a separation wall (6),
    b) a pair of nasal prongs (5) in fluid communication with the first compartment (1),
    c) the first compartment (1) comprising a first inlet (11) configured to conduct a first gas into said first compartment (1),
    d) the second compartment (2) comprising a second inlet (2) configured to conduct a second gas into said second compartment (2), and
    e) the separation wall (6) comprising at least one valve element (3) configured to
        permit the passage of gas from the second compartment (2) to the first compartment (1) and
        prevent or limit the passage of gas from the first compartment (1) to the second compartment (2).

3. The Nitric Oxide for use in the treatment of pulmonary vasoconstriction by inhalation from a nasal cannula assembly (10) of Numbered Sentence 1 or 2, wherein the patient is an adult, an infant or a newborn.

4. The Nitric Oxide for use in the treatment of pulmonary vasoconstriction by inhalation from a nasal cannula assembly (10) of Numbered Sentence 1, 2 or 3, wherein the patient has pulmonary vasoconstriction associated with persistent pulmonary hypertension of the newborn.

5. The Nitric Oxide for use in the treatment of pulmonary vasoconstriction by inhalation from a nasal cannula assembly (10) of Numbered Sentence 1, 2, 3 or 4, wherein the patient has pulmonary vasoconstriction is associated with pulmonary arterial hypertension.

6. The Nitric Oxide for use in the treatment of pulmonary vasoconstriction by inhalation from a nasal cannula assembly (10) of Numbered Sentence 1, 2, 3, 4 or 5, wherein the NO-containing gas is mixed with an oxygen-containing gas just before being inhaled by the patient.

7. The Nitric Oxide for use in the treatment of pulmonary vasoconstriction by inhalation from a nasal cannula assembly (10) of Numbered Sentence 1, 2, 3, 4, 5 or 6, wherein the NO-containing gas is a NO/nitrogen mixture.

8. The Nitric Oxide for use in the treatment of pulmonary vasoconstriction by inhalation from a nasal cannula assembly (10) of Numbered Sentence 1, 2, 3, 4, 5, 6 or 7, wherein the NO-containing gas consists in a NO/nitrogen mixture containing from 1 ppm to 5000 ppmv of NO.

9. The Nitric Oxide for use in the treatment of pulmonary vasoconstriction by inhalation from a nasal cannula assembly (10) of Numbered Sentence 1, 2, 3, 4, 5, 6, 7 or 8, wherein the $O_2$-containing gas is air or an $O_2/N_2$ mixture containing at least 21% (by volume) of $O_2$.

10. The Nitric Oxide for use in the treatment of pulmonary vasoconstriction by inhalation from a nasal cannula assembly (10) according to Numbered Sentence 1, 2, 3, 4, 5, 6, 7, 8 or 9, wherein the separation wall (6) comprises at least two valve elements (3).

11. The Nitric Oxide for use in the treatment of pulmonary vasoconstriction by inhalation from a nasal cannula assembly (10) of Numbered Sentence 1, 2, 3, 4, 5, 6, 7, 8, 9 or 10, wherein the first compartment (1) comprises a first inlet (11) forming a side gases entry in fluid communication with a gas transport conduct.

12. The Nitric Oxide for use in the treatment of pulmonary vasoconstriction by inhalation from a nasal cannula assembly (10) of Numbered Sentence 1, 2, 3, 4, 5, 6, 7, 8, 9, 10 or 11, wherein the nasal cannula assembly further comprises a hollow body (4) comprising an internal chamber (7) comprising at least the first compartment (1).

13. The Nitric Oxide for use in the treatment of pulmonary vasoconstriction by inhalation from a nasal cannula assembly (10) of Numbered Sentence 1, 2, 3, 4, 5, 6, 7, 8, 9, 11 or 12, wherein at least the first compartment (1) is part of a hollow body (4) configured to be capable of acting as a gas conduct or a gas manifold.

14. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12 or 13, wherein the hollow body (4) and said pair of nasal prong (5) are integrally molded from a soft plastics material.

15. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13 or 14, wherein the prongs (5) are detachable from said hollow body (4) and selected from different sized prongs suitable for different sized patient nares.

16. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14 or 15, wherein the valve elements (3) are one-way valves.

17. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 15 or 16, wherein a pair of valve elements (3) is arranged in the separation wall (6), directly opposite the pair nasal prongs (5).

18. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 15, 16 or 17, wherein the second compartment (2) comprises a deformable wall (14).

19. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 16, 17 or 18, wherein the second compartment (2) forms a deformable-wall reservoir comprising a fully inflated internal volume for the gas of about 0.5 to 5 ml.

20. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 16, 17, 18 or 19, wherein the nasal cannula assembly does not comprise a sensor configured to detect an onset of patient inspiration.

21. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 16, 17, 18, 19 or 20, wherein the valve (3) is selected from an umbrella valve or a duckbill valve.

22. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 16, 17, 18, 19, 20 or 21, wherein the valve (3) has a cracking pressure of 0.5 kPa or less.

23. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 16, 17, 18, 19, 20, 21 or 22, wherein the reservoir (2) has a greater Compliance while filling than when the reservoir (2) is full.

24. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 16, 17, 18, 19, 20, 21, 22, or 23, wherein the nasal prongs (5) includes an external pillow element (8) at an end.

25. The Nitric Oxide for use in the treatment of pulmonary vasoconstriction by inhalation from a nasal cannula assembly (10) of Numbered Sentence 24, wherein the pillow elements (8) is made of silicone.

26. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 16, 17, 18, 19, 20, 21, 22, 23, 24 or 25, wherein the nasal cannula assembly further comprises an expiratory orifice (13), optionally comprising an additional one-way expiratory valve, between the first compartment (1) defining an internal chamber (7) and an external atmosphere.

27. The Nitric Oxide for use in the treatment of pulmonary vasoconstriction by inhalation from a nasal cannula assembly (10) of Numbered Sentence 1, 2, 3, 4, 5, 6, 7, 8, 9, 10, 11, 12, 13, 14, 16, 17, 18, 19, 20, 21, 22, 23, 24, 25 or 26, wherein the nasal cannula assembly further comprises a resistive element (9) between an internal volume (7) of the first compartment (1) and an air or oxygen supply (11), the resistive element configured to ensure a sufficient pressure drop upon the onset of inhalation to open at least one valve element (3).

The invention may be further defined in some embodiments by one or more of the following numbered sentences:

1. Use of Nitric Oxide in the manufacture of a medicament for the treatment of pulmonary vasoconstriction by inhalation from a nasal cannula assembly (10) adapted to deliver gases to a patient, the nasal cannula assembly (10) comprising:
   A) a hollow body (4) configured to be capable of acting as a gas conduct or a gas manifold and comprising an internal chamber (7) defining a first compartment (1),
   B) the first compartment (1) and a second compartment (2) separated by a separation wall (6),
   C) a pair of nasal prongs (5) in fluid communication with the first compartment (1),
   D) the first compartment (1) comprising a first inlet (11) forming a side gases entry in fluid communication with a gas transport conduct and configured to conduct a first gas into said first compartment (1),
   E) the second compartment (2) having a fully inflated internal volume for a gas of about 0.5 to 5 ml, the second compartment (2) comprising,
      a second inlet (12) configured to conduct a second gas into said second compartment (2), and
      a deformable wall (14),
   F) the separation wall (6) comprising at least two, one-way, duckbill or umbrella valves (3) having a cracking pressure of 0.5 kPa or less which are oriented and arranged in the separation wall (6) directly opposite the pair nasal prongs (5) to thereby be capable of
      permitting a passage of gas from the second compartment (2) to the first compartment (1) and preventing or limiting a passage of gas from the first compartment (1) to the second compartment (2),
  a) the nasal cannula assembly (10) fluidly connected to a source of NO-containing gas having from 1 ppm to 5000 ppm in volume of NO in a balance of nitrogen, and
  b) the nasal cannula assembly (10) fluidly connected to a source of an oxygen-containing gas containing at least 21% (by volume) of $O_2$ in fluid communication with the nasal cannula assembly (10).

2. Use of Nitric Oxide in the manufacture of a medicament Nitric Oxide for the treatment of pulmonary vasoconstriction by inhalation from a nasal cannula assembly (10), wherein the nasal cannula assembly (10) comprises:
  a) a first compartment (1) and a second compartment (2) separated by a separation wall (6),
  b) a pair of nasal prongs (5) in fluid communication with the first compartment (1),
  c) the first compartment (1) comprising a first inlet (11) configured to conduct a first gas into said first compartment (1),
  d) the second compartment (2) comprising a second inlet (2) configured to conduct a second gas into said second compartment (2), and
  e) the separation wall (6) comprising at least one valve element (3) configured to
    permit the passage of gas from the second compartment (2) to the first compartment (1) and
    prevent or limit the passage of gas from the first compartment (1) to the second compartment (2).

3. The manufacturing process of Numbered Sentence 1 or 2, wherein the patient is an adult, an infant or a newborn.

4. The Manufacturing process of Numbered Sentence 1, 2 or 3, wherein the patient has pulmonary vasoconstriction associated with persistent pulmonary hypertension of the newborn.

5. The Manufacturing process of Numbered Sentence 1, 2, 3 or 4, wherein the patient has pulmonary vasoconstriction is associated with pulmonary arterial hypertension.

6. The Manufacturing process of Numbered Sentence 1, 2, 3, 4 or 5, wherein the NO-containing gas is mixed with an oxygen-containing gas just before being inhaled by the patient.

7. The Manufacturing process of Numbered Sentence 1, 2, 3, 4, 5 or 6, wherein the NO-containing gas is a NO/nitrogen mixture.

8. The Manufacturing process of Numbered Sentence 1, 2, 3, 4, 5, 6 or 7, wherein the NO-containing gas consists in a NO/nitrogen mixture containing from 1 ppm to 5000 ppmv of NO.

9. The Manufacturing process of Numbered Sentence 1, 2, 3, 4, 5, 6, 7 or 8, wherein the $O_2$-containing gas is air or an $O_2/N_2$ mixture containing at least 21% (by volume) of $O_2$.

10. The Manufacturing process according to Numbered Sentence 1, 2, 3, 4, 5, 6, 7, 8 or 9, wherein the separation wall (6) comprises at least two valve elements (3).

11. The Manufacturing process of Numbered Sentence 1, 2, 3, 4, 5, 6, 7, 8, 9 or 10, wherein the first compartment (1) comprises a first inlet (11) forming a side gases entry in fluid communication with a gas transport conduct.

12. The Manufacturing process of Numbered Sentence 1, 2, 3, 4, 5, 6, 7, 8, 9, 10 or 11, wherein the nasal cannula assembly further comprises a hollow body (4) comprising an internal chamber (7) comprising at least the first compartment (1).

13. The Manufacturing process of Numbered Sentence 1, 2, 3, 4, 5, 6, 7, 8, 9, 11 or 12, wherein at least the first compartment (1) is part of a hollow body (4) configured to be capable of acting as a gas conduct or a gas manifold.

14. The Manufacturing process of Numbered Sentence 1, 2, 3, 4, 5, 6, 7, 8, 9, 10, 11, 12 or 13, wherein the hollow body (4) and said pair of nasal prong (5) are integrally molded from a soft plastics material.

15. The Manufacturing process of Numbered Sentence 1, 2, 3, 4, 5, 6, 7, 8, 9, 10, 11, 12, 13 or 14, wherein the prongs (5) are detachable from said hollow body (4) and selected from different sized prongs suitable for different sized patient nares.

16. The Manufacturing process of Numbered Sentence 1, 2, 3, 4, 5, 6, 7, 8, 9, 10, 11, 12, 13, 14 or 15, wherein the valve elements (3) are one-way valves.

17. The Manufacturing process of Numbered Sentence 1, 2, 3, 4, 5, 6, 7, 8, 9, 10, 11, 12, 13, 14, 15 or 16, wherein a pair of valve elements (3) is arranged in the separation wall (6), directly opposite the pair nasal prongs (5).

18. The Manufacturing process of Numbered Sentence 1, 2, 3, 4, 5, 6, 7, 8, 9, 10, 11, 12, 13, 14, 15, 16 or 17, wherein the second compartment (2) comprises a deformable wall (14).

19. The Manufacturing process of Numbered Sentence 1, 2, 3, 4, 5, 6, 7, 8, 9, 10, 11, 12, 13, 14, 16, 17 or 18, wherein the second compartment (2) forms a deformable-wall reservoir comprising a fully inflated internal volume for the gas of about 0.5 to 5 ml.

20. The Manufacturing process of Numbered Sentence 1, 2, 3, 4, 5, 6, 7, 8, 9, 10, 11, 12, 13, 14, 16, 17, 18 or 19, wherein the nasal cannula assembly does not comprise a sensor configured to detect an onset of patient inspiration.

21. The Manufacturing process of Numbered Sentence 1, 2, 3, 4, 5, 6, 7, 8, 9, 10, 11, 12, 13, 14, 16, 17, 18, 19 or 20, wherein the valve (3) is selected from an umbrella valve or a duckbill valve.

22. The Manufacturing process of Numbered Sentence 1, 2, 3, 4, 5, 6, 7, 8, 9, 10, 11, 12, 13, 14, 16, 17, 18, 19, 20 or 21, wherein the valve (3) has a cracking pressure of 0.5 kPa or less.

23. The Manufacturing process of Numbered Sentence 1, 2, 3, 4, 5, 6, 7, 8, 9, 10, 11, 12, 13, 14, 16, 17, 18, 19, 20, 21 or 22, wherein the reservoir (2) has a greater Compliance while filling than when the reservoir (2) is full.

24. The Manufacturing process of Numbered Sentence 1, 2, 3, 4, 5, 6, 7, 8, 9, 10, 11, 12, 13, 14, 16, 17, 18, 19, 20, 21, 22, or 23, wherein the nasal prongs (5) includes an external pillow element (8) at an end.

25. The Manufacturing process of Numbered Sentence 24, wherein the pillow elements (8) is made of silicone.

26. The Manufacturing process of Numbered Sentence 1, 2, 3, 4, 5, 6, 7, 8, 9, 10, 11, 12, 13, 14, 16, 17, 18, 19, 20, 21, 22, 23, 24 or 25, wherein the nasal cannula assembly further comprises an expiratory orifice (13), optionally comprising an additional one-way expiratory valve, between the first compartment (1) defining an internal chamber (7) and an external atmosphere.

27. The Manufacturing process of Numbered Sentence 1, 2, 3, 4, 5, 6, 7, 8, 9, 10, 11, 12, 13, 14, 16, 17, 18, 19, 20, 21, 22, 23, 24, 25 or 26, wherein the nasal cannula assembly further comprises a resistive element (9) between an internal volume (7) of the first compartment (1) and an air or oxygen supply (11), the resistive element configured to ensure a sufficient pressure drop upon the onset of inhalation to open at least one valve element (3).

BRIEF DESCRIPTION OF THE SEVERAL VIEWS OF THE DRAWINGS

The present invention will be better understood thanks to the following description and explanation made in reference to the Figures, wherein.

DETAILED DESCRIPTION OF THE INVENTION

Figure 1:
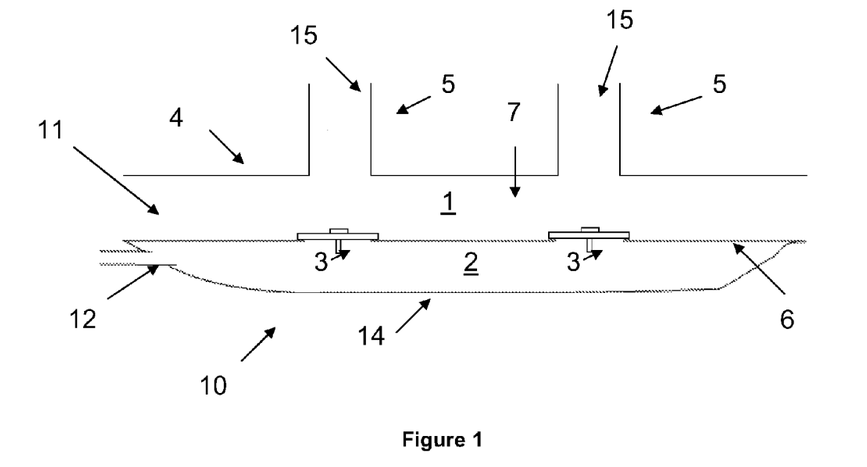
FIG. 1 is a schematic of a first embodiment of a nasal cannula assembly according to the present invention.

A schematic of a first embodiment of the nasal cannula assembly of the present invention is shown in FIG. 1 (in cross section).

The nasal cannula assembly of the present invention is a patient interface generally comprising a pair of nasal prongs 5 coupled indirectly to a deformable-wall 14 having a valved 3 reservoir 2 supplied with NO contained in nitrogen (12), e.g. at 225, 450, 800 or 1000 ppm in volume.

The pair of nasal prongs 5 is positioned on a hollow body 4, for example, an air or oxygen conduit or manifold, comprising an internal hollow volume or chamber 7 thereby forming a first compartment 1 that receives the gases.

The nasal prongs 5 are small conduits or tubes adapted for insertion into the nares of a patient and through which passes the gas mixture that is subsequently inhaled by the patient. Each prong 5 comprises an outlet orifice 15 at its end.

The hollow body 4 can be made of a rigid light material, such as polymer or similar. Preferably, the hollow body 4 and the pair of nasal prong 5 are integrally molded from a soft plastics material. However, the prongs 5 can also be detachable from said hollow body 4 to allow different sized prongs to be placed on said hollow body 4 to suit different sized patients, such as adults and infants. The hollow body 4 is in turn in fluid communication with valved 3 reservoir 2 formed by the deformable-wall 14 and separation wall 6. In other words, the nasal cannula assembly of the present invention is split into two main inhaled gas compartments 1 and 2 that are separated each from the other by a separation wall 6.

The second compartment 2 forms a deformable reservoir receiving the NO gas through an inlet 12. The deformable wall 14 of the reservoir or second compartment 2 should be made from a thin, flexible sheet of polymer material so that the reservoir readily inflates during exhalation when the valves 3 are closed, but collapses, at the start of inhalation, after the valves 3 open. In this manner, NO-containing gas is allowed to accumulate in the reservoir while the patient exhales, and then is released as a bolus at the start of inhalation as the reservoir collapses and its contents empty through the valves 3 into the first compartment 1. Throughout this cycle a constant flow of NO-containing gas may be maintained through the inlet 12.

The second compartment 2 fluidly communicates with the first compartment 1 through one or more fluid transfer elements such as the exemplary one-way valves 3 which may be for instance the two umbrella valves 3 shown in FIG. 1. These fluid transfer elements are arranged in the separation wall 6. Preferably, as shown in FIG. 1, two valves 3 are positioned along the conduit 7 forming the hollow main body 4, directly opposite the nasal prongs 5, i.e. each valve 3 is facing one nasal prong 5, so as to facilitate the gas circulation from the second compartment 2 to the first compartment 1 and subsequently to the nasal prongs 5.

The fluid transfer elements may be umbrella valves, duckbill valves, valve-like conduits or flow constrictions apertures designed to permit gas flow from the second compartment 2 to the first compartment 1, but to resist flow in the opposite direction from the first compartment 1 to the second compartment 2. In embodiments having valves 3, the valves preferably respond to any drop in ambient pressure (i.e. due to inhalation). Ideally, valve 3 is selected to have a "cracking pressure" of zero or at least as low as is mechanically feasible. Any inhalation flow through nare tubes 5 should preferably result in valve 3 opening.

In any case, the combination of valves 3 and deformable wall 14 of the embodiment depicted in FIG. 1 should be responsive to increases and decreases in pressure that develop during exhalation and inhalation, respectively, so as to allow the deformable reservoir 2 to inflate with NO-containing gas during exhalation, and then empty to release this gas through the valves 3 into the first compartment 1 during inhalation.

Generally the deformable wall 14 needs to be of a thin, flexible material such that zero or near zero positive pressure above atmospheric develops in compartment 2 as it fills from the Nitric Oxide flow 12 during exhalation (so that the valves stay closed while the bag fills). Reservoir 2 thus should be designed preferably to have infinite or near infinite Compliance (where Compliance=deltaVolume/deltaPressure), while filling—and then drop to zero or near zero Compliance once full.

The first compartment 1 is supplied with an oxygen-containing gas through a first inlet port 11, whereas the second compartment 2 forming a NO-reservoir is supplied with a constant flow of NO-containing gas through a second inlet port 12.

During patient exhalation, the valves 3 close, so that the second compartment or reservoir 2 fills with NO containing gas, whereas, during patient inhalation, the valves 3 open so that NO-containing gas mixes with air and/or oxygen in the first compartment 1 as it is inhaled by the patient through the prongs 5.

The volume of the second compartment 2 is configured and sized so as to be small compared to the patient's inhaled tidal volume, so that the second compartment 2 quickly empties during the initial period of the inhalation phase to create a bolus of elevated NO concentration at the start of the inhalation.

Normally high concentrations of NO, e.g. 800 vol. ppm of NO in nitrogen, are delivered to the second compartment 2 from a source of $NO/N_2$, such as a gas cylinder with integrated pressure regulator and flow metering apparatus.

Patient safety is ensured by supplying only low flows of NO-containing gas. For example, to deliver to the patient an amount of NO equivalent to that delivered during continuous supply of gas containing 5 ppmv NO throughout the duration of a 500 ml tidal breath, about 3 ml of gas containing 800 ppmv NO should be supplied each breath.

During tidal breathing, the expiratory time of a typical adult will range from approximately 2 to 5 seconds. Therefore, supply flows on the order of 1 ml/s of NO containing gas are required. In operation, the NO flow rate may be adjusted based on visual inspection of the inflation/deflation of deformable wall 14 to ensure the appropriate flow rate for a specific patient's inhalation pattern.

Figure 3:
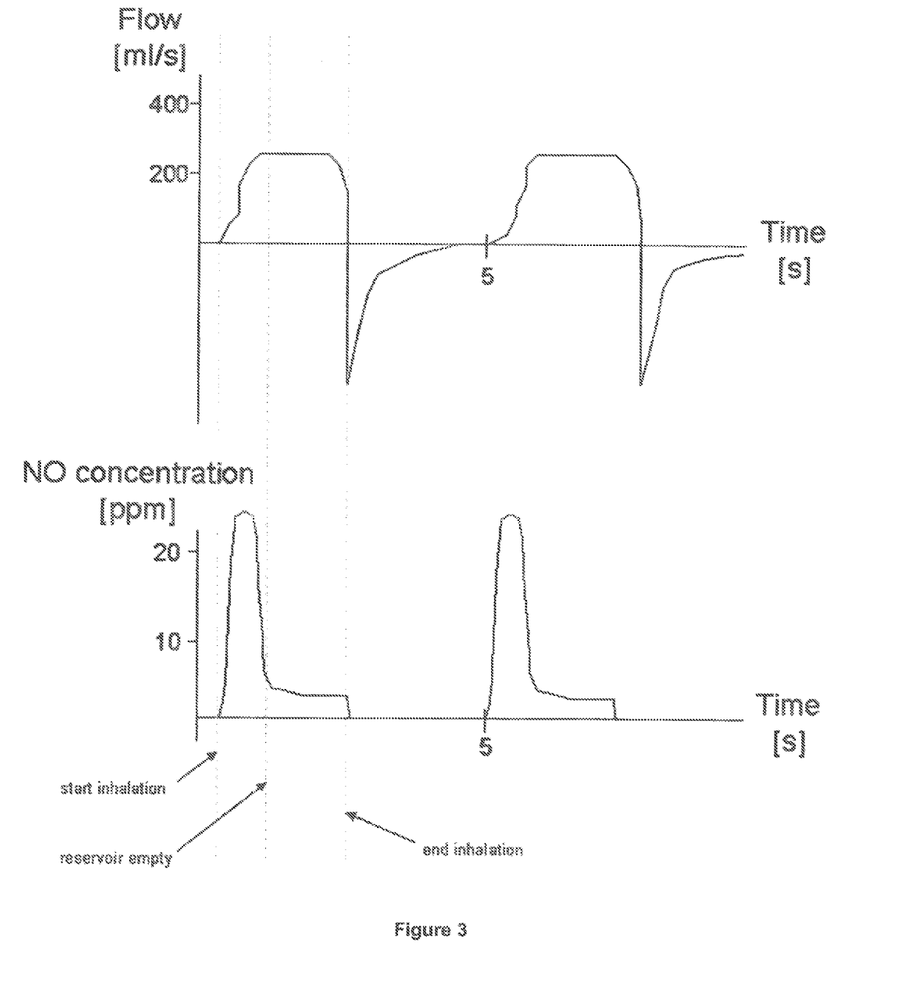

FIG. 3 displays an estimated pattern of inhaled NO concentration that would be achieved using the present invention based on the numbers mentioned above.

More precisely, one can see on FIG. 3 the estimated tidal flow and inhaled NO concentration curves during a typical adult tidal breathing pattern using a nasal cannula assembly 10 according to the present invention supplied with 1 ml/sec flow of gas containing 800 ppmv of NO in $N_2$.

The breathing pattern is shown in the upper curve, with positive flow representing inhalation, and negative flow representing exhalation. The estimated NO concentration contained in the gas mixture delivered to the patient through the nasal prongs 5 during the inhalation phase of the breathing cycle is shown in the lower curve.

The NO concentration spikes at the start of inhalation as NO-containing gas is released from the second compartment 2 before rapidly decreasing once the second compartment empties.

Through the later stages of inhalation a low NO concentration is delivered as fresh NO-containing gas supplied through inlet 12 passes into the first chamber 1 and the nasal prongs 5.

In contrast, throughout exhalation, flow of NO-containing gas from the second chamber to the first chamber is prevented by the valves 3.

For some patients, it may be desirable to minimize gas leaks between the nasal prongs 5 and the patient's nares, e.g. to provide continuous positive airway pressure CPAP, Bi-level positive airway pressure (Bi-PAP), or other positive pressure support in combination with NO therapy, or to ensure the proper opening and closing function of the valves 3.

Figure 2:
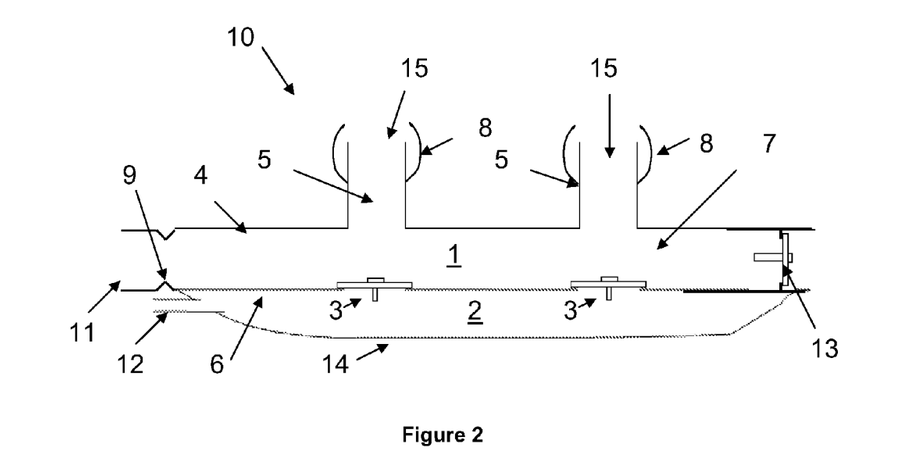
FIG. 2 is a schematic of a second embodiment of a nasal cannula assembly according to the present invention, and FIG. 3 displays an estimated pattern of inhaled NO concentration that could be achieved using a nasal cannula assembly according to the present invention.

In such circumstances, the nasal cannula assembly 10 may comprise additional elements as shown in FIG. 2.

First, each of the nasal prongs 5 includes an external pillow element 8 at its ends, which is intended to more tightly secure the prongs 5 inside the patient's nares or nostrils. Said pillow elements 8 can be made of soft resilient material, such as silicone or similar.

Second, an additional one-way expiratory valve 13 or expiratory orifice is included between the first compartment 1 defining the internal chamber 7 and the room atmosphere.

Additionally, a resistive element 9 may optionally be placed between the internal volume 7 of the first compartment 1 and the air or oxygen supply conduit to ensure a sufficient pressure drop upon the onset of inhalation to open valves 3.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising").

"Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A method for treating pulmonary vasoconstriction in a patient, comprising:
  a) providing a nasal cannula assembly (10) adapted to deliver gases to the patient, the nasal cannula assembly (10) comprising:
    A) a hollow body (4) configured to be capable of acting as a gas conduct or a gas manifold and comprising an internal chamber (7) defining a first compartment (1),
    B) the first compartment (1) and a second compartment (2) separated by a separation wall (6),
    C) a pair of nasal prongs (5) in fluid communication with the first compartment (1),
    D) the first compartment (1) comprising a first inlet (11) forming a side gases entry in fluid communication with a gas transport conduct and configured to conduct a first gas into said first compartment (1),
    E) the second compartment (2) having a fully inflated internal volume for a gas of about 0.5 to 5 ml, the second compartment (2) comprising,
      a second inlet (12) configured to conduct a second gas into said second compartment (2), and
      a deformable wall (14) having a greater compliance while filling than when the second compartment (2) is full,
    F) the separation wall (6) comprising two, one-way, duckbill or umbrella valves (3) a cracking pressure of 0.5 kPa or less which are oriented and arranged in the separation wall (6) directly opposite the pair of nasal prongs (5) to thereby be capable of
      permitting a passage of gas from the second compartment (2) to the first compartment (1) and
      preventing or limiting a passage of gas from the first compartment (1) to the second compartment (2),
  b) providing a source of NO-containing gas having from 1 ppm to 5000 ppm in volume of NO in a balance of nitrogen in fluid communication with the nasal cannula assembly (10),
  c) providing a source of an oxygen-containing gas containing at least 21% (by volume) of $O_2$ in fluid communication with the nasal cannula assembly (10), and
  d) providing a therapeutically-effective amount of the NO-containing gas to said patient through said nasal cannula assembly for inhalation.

2. The method according to claim 1, wherein the patient is an adult, an infant or a newborn.

3. The method according to claim 1, wherein the patient is a newborn and has pulmonary vasoconstriction associated with persistent pulmonary hypertension.

4. The method according to claim 1, wherein the patient has pulmonary vasoconstriction associated with pulmonary arterial hypertension.

5. The method according to claim 1, wherein the hollow body (4) and said pair of nasal prongs (5) are integrally molded from a soft plastics material.

6. The method according to claim 1, wherein the pair of nasal prongs (5) are detachable from said hollow body (4) and selected from different sized prongs suitable for different sized patient nares.

7. The method according to claim 1, wherein the nasal cannula assembly does not comprise a sensor configured to detect an onset of patient inspiration.

8. The method according to claim 1, wherein the pair of nasal prongs (5) includes an external pillow element (8) at an end.

9. The method according to claim 8, wherein the external pillow element (8) is made of silicone.

10. The method according to claim 1, wherein the nasal cannula assembly further comprises an expiratory orifice (13) in the first compartment (1) defining a fluid communication path from an internal chamber (7) to an external atmosphere.

* * * * *